United States Patent
Kabra

(10) Patent No.: US 8,754,123 B2
(45) Date of Patent: *Jun. 17, 2014

(54) PHARMACEUTICAL COMPOSITIONS HAVING DESIRABLE BIOAVAILABILITY

(75) Inventor: Bhagwati P. Kabra, Euless, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 67 days.

This patent is subject to a terminal disclaimer.

(21) Appl. No.: 13/442,475

(22) Filed: Apr. 9, 2012

(65) Prior Publication Data

US 2012/0245227 A1    Sep. 27, 2012

Related U.S. Application Data

(63) Continuation of application No. 12/403,529, filed on Mar. 13, 2009, now Pat. No. 8,178,582.

(60) Provisional application No. 61/037,117, filed on Mar. 17, 2008, provisional application No. 61/111,920, filed on Nov. 6, 2008.

(51) Int. Cl.
| | |
|---|---|
| *A01N 37/08* | (2006.01) |
| *A61K 31/215* | (2006.01) |
| *A61K 9/00* | (2006.01) |
| *A61K 31/5575* | (2006.01) |
| *A61K 47/44* | (2006.01) |

(52) U.S. Cl.
CPC ........... *A61K 9/0048* (2013.01); *A61K 31/5575* (2013.01); *A61K 47/44* (2013.01)
USPC ....................................................... 514/530

(58) Field of Classification Search
CPC .. A61K 9/0048; A61K 31/5575; A61K 47/44
USPC ....................................................... 514/530
See application file for complete search history.

(56) References Cited

U.S. PATENT DOCUMENTS

| | | | |
|---|---|---|---|
| 3,931,319 A | 1/1976 | Green et al. | |
| 4,027,020 A | 5/1977 | Green et al. | |
| 4,407,791 A | 10/1983 | Stark | |
| 4,522,806 A | 6/1985 | Muhlemann et al. | |
| 4,525,346 A | 6/1985 | Stark | |
| 4,836,986 A | 6/1989 | Ogunbiyi et al. | |
| 5,037,647 A | 8/1991 | Chowhan et al. | |
| 5,221,664 A | 6/1993 | Berkowitz et al. | |
| 5,300,287 A | 4/1994 | Park | |
| 5,320,843 A | 6/1994 | Rahega et al. | |
| 5,631,287 A | 5/1997 | Schneider | |
| 5,741,817 A | 4/1998 | Chowhan et al. | |
| 5,817,277 A | 10/1998 | Mowrey-McKee et al. | |
| 5,932,572 A | 8/1999 | Dean et al. | |
| 6,017,861 A | 1/2000 | Fujiwara et al. | |
| 6,034,043 A | 3/2000 | Fujiwara et al. | |
| 6,235,781 B1 * | 5/2001 | Weiner et al. ................. | 514/530 |
| 6,319,464 B1 | 11/2001 | Asgharian | |
| 6,348,190 B1 | 2/2002 | Illes et al. | |
| 6,482,799 B1 | 11/2002 | Tusé et al. | |
| 6,503,497 B2 | 1/2003 | Chowhan et al. | |
| 6,743,439 B1 * | 6/2004 | Castillo et al. ................. | 424/427 |
| 7,851,504 B2 | 12/2010 | Chang et al. | |
| 8,084,501 B2 | 12/2011 | Deaciuc et al. | |
| 8,178,582 B2 * | 5/2012 | Kabra ........................... | 514/570 |
| 2002/0122831 A1 | 9/2002 | Mowrey-McKee et al. | |
| 2002/0174765 A1 | 11/2002 | Matsuda et al. | |
| 2004/0082660 A1 | 4/2004 | Ueno | |
| 2007/0051362 A1 * | 3/2007 | Sullivan et al. .......... | 128/200.23 |
| 2007/0248697 A1 | 10/2007 | Morishima et al. | |
| 2008/0093247 A1 | 4/2008 | Han et al. | |
| 2009/0234004 A1 | 9/2009 | Kabra | |
| 2009/0234013 A1 | 9/2009 | Kabra | |
| 2011/0152264 A1 | 6/2011 | Reunamaki et al. | |
| 2012/0029073 A1 * | 2/2012 | Kabra et al. .................. | 514/530 |

FOREIGN PATENT DOCUMENTS

| | | | |
|---|---|---|---|
| EP | 1547599 | 6/2005 | |
| EP | 2123278 A1 | 11/2009 | |
| JP | 2002332225 | 11/2002 | |
| JP | 2003-104870 | 4/2003 | |
| JP | 2005170795 | 6/2005 | |
| JP | 2005247801 | 9/2005 | |
| WO | 91/09523 | 7/1991 | |
| WO | 9614829 | 5/1996 | |
| WO | 9729752 | 8/1997 | |
| WO | 98/19680 | 5/1998 | |
| WO | WO98/19680 * | 5/1998 | ........... A61K 31/557 |
| WO | 98/25620 | 6/1998 | |
| WO | 98/41208 | 9/1998 | |
| WO | 98/53809 | 12/1998 | |
| WO | 00/03736 | 1/2000 | |
| WO | 2004037267 A1 | 5/2004 | |
| WO | 2009/117316 | 9/2009 | |

OTHER PUBLICATIONS

Alward W., 1998, N Engl. J. Med., "Medical Management of Glaucoma", 339; 1298; 1300-1306.

Feldman et al., 2007, Ophthalmology, "Comparison of the Ocular Hypotensive Efficacy of Adjunctive Brimonidine 0.15% or Brinzolamide 1% in Combination with Travoprost 0.004%", 114(7):1248-1254.

Guidance for Industry: Container Closure Systems for Packaging Human Drugs and Biologics, U.S. Department of Health and Human Services, Food and Drug Administration, May 1999.

PCT International Search Report for corresponding International Application No. PCT/US2009/037077 with mailing date Jul. 20, 2010.

(Continued)

*Primary Examiner* — Sean Basquill
(74) *Attorney, Agent, or Firm* — Scott A. Chapple

(57) ABSTRACT

The present invention is directed to the provision of pharmaceutical compositions. The compositions include a therapeutic agent and a relatively low amount of surfactant for providing higher bioavailability of the therapeutic agent. The compositions are particularly desirable as ophthalmic compositions in which the therapeutic agent is a prostaglandin such as travoprost and the surfactant is a vegetable oil such as castor oil.

23 Claims, 6 Drawing Sheets

(56) References Cited

OTHER PUBLICATIONS

PCT Written Opinion for corresponding International Application No. PCT/US2009/037077 with mailing date Jul. 20, 2010.

Pawar and Majumdar, 2006, AAPS PharmSciTech, "Effect of Formulation Factors on In Vitro Permeation of Moxifloxacin From Aqueous Drops Through Excised Goat, Sheep, and Buffalo Corneas", 7(1):E1-E6.

Ammar et al., 2010, "Effects of Benzalkonium Chloride-preserved, Polyquad-Preserved, and sofZia-Preserved Topical Glaucoma Medications on Human Ocular Epithelial Cells", Ad. Ther., 27(11), 1-9.

Ayaki et al., 2010, "Toxicity of antiglaucoma drugs with and without benzalkonium chloride to cultured human corneal endothelia cells", Clinical Ophthlamology,4, 1217-1222.

Baudouin et al., 2007, IVOS, "In vitro Studies of Antiglaucomatous Prostaglandin Analogues: Travoprost with and without Benzalkonium Chloride and Preserved Latanoprost", vol. 48(9), 4123-4128.

European Patent Office, Communication Pursuant to Rule 114(2) EPC, Application No. 09722278.0, May 8, 2013, 4 pgs.

European Patent Office, Communication Pursuant to Rule 114(2) EPC, Application No. 09722278.0, Feb. 19, 2014, 5 pgs.

\* cited by examiner

PHARMACEUTICAL COMPOSITIONS HAVING DESIRABLE BIOAVAILABILITY

CROSS-REFERENCE TO RELATED APPLICATIONS

The present application is a continuation of U.S. Ser. No. 12/403,529, filed Mar. 13, 2009 now U.S. Pat. No. 8,178,582, which claims priority based on U.S. Provisional Patent Application Ser. No. 61/037,117 filed Mar. 17, 2008, and U.S. Provisional Patent Application Ser. No. 61/111,920, filed Nov. 6, 2008.

TECHNICAL FIELD OF THE INVENTION

The present invention is related to pharmaceutical compositions that contain surfactant concentrations that promote bioavailability of a therapeutic agent in the composition. More specifically the present invention relates to topical pharmaceutical compositions (e.g., multi-dose ophthalmic compositions) having relatively low concentrations of surfactant that promote the bioavailability of a therapeutic agent (e.g., a prostaglandin such as travoprost).

BACKGROUND OF THE INVENTION

The present invention is directed to pharmaceutical compositions formulated to exhibit enhanced bioavailability of a therapeutic agent of the composition. The composition may also exhibit other additional or alternative desired characteristics. For example, the composition may also be sterile, may exhibit desired antimicrobial or preservation efficacy, may exhibit a desired degree of stability, combinations thereof or the like.

Therapeutic agents (e.g., ophthalmic drugs) of many pharmaceutical compositions are often required to be stable within those compositions. It is typically undesirable for the therapeutic agents or overall compositions to decompose or chemically or physically change to a significant degree prior to application of the agents to an individual or otherwise. For maintaining stability, pharmaceutical compositions are typically formulated with ingredients that can enhance such stability or ingredients that can minimize destabilizing effects of other entities (e.g., chemicals, ambient conditions or the like).

Surfactants are one preferred family of ingredients that have exhibited significant efficacy in stabilizing pharmaceutical compositions and/or therapeutic agents thereof (particularly aqueous ophthalmic solutions including relatively lipophilic and/or relatively insoluble components). Moreover, it has generally been believed that stability of an agent or composition can often be achieved by using larger concentrations of surfactant within that pharmaceutical composition.

In addition to stability of the agents or compositions, it is also typically desirable for the therapeutic agents of the pharmaceutical compositions to exhibit relatively high degrees of bioavailability. Such bioavailability often becomes particularly important where the method or manner of application or dosing of a particular pharmaceutical composition provides only a limited amount of time for the therapeutic agent of that composition to be absorbed or otherwise taken in by a biological target such as an eye, ear, throat or nose of an individual. As an example, topically applied ophthalmic pharmaceutical compositions may only dwell in or on an individual's eye for a limited period of time (e.g., before tears transport the composition elsewhere). Thus, it is often desirable to limit the concentration of any ingredient in a pharmaceutical composition where that ingredient tends to inhibit bioavailability of a therapeutic agent of that composition.

Recently, it has been discovered that surfactants, when used at certain higher concentrations, may act as an ingredient that can limit the bioavailability of a therapeutic agent, particularly an ophthalmic therapeutic agent. As a consequence, the addition of surfactant to pharmaceutical compositions and particularly ophthalmic compositions can limit the bioavailability and, in turn, the efficacy of the therapeutic agent in the composition. However, as suggested above, surfactants can also be quite desirable in a pharmaceutical composition since they can significantly enhance the stability of a pharmaceutical composition or therapeutic agent.

In view of the above, it would be desirable to provide a pharmaceutical composition with a lower surfactant concentration and/or a higher bioavailability of a therapeutic agent. Moreover, it would also be desirable, although not required unless otherwise specifically stated, for such composition to exhibit a desirable level of stability.

SUMMARY OF THE INVENTION

Accordingly, the present invention is directed to a pharmaceutical composition, particularly an ophthalmic composition, that combines a therapeutic agent with a relatively low surfactant concentration. Typically, the composition will exhibit a higher bioavailability of the therapeutic agent particularly when used for topical applications. In one embodiment, an effectively low amount of surfactant is provided such that an area under a concentration/time curve when determined for the pharmaceutical composition of the present invention as applied to a biological target is at least 130%, more typically at least 200% and even possibly at least 250% relative to an area under a similar concentration/time curve when determined for a control composition as applied to the biological target. For such embodiment, the control composition will typically have at least double the amount of surfactant relative to the pharmaceutical composition.

The present invention has been found particularly suitable for use in ophthalmic compositions and more particularly multi-dose ophthalmic solutions, which tend to be aqueous, but may be otherwise. One exemplary combination of therapeutic agent and surfactant for such compositions is the combination of a prostaglandin (e.g., travoprost) with an ethoxylated and/or hydrogenated vegetable oil (e.g., Polyoxyl 40 Hydrogenated castor oil). In such a combination, the amount of surfactant is typically below about 0.4 w/v % of the composition and the amount of therapeutic agent is typically below about 0.01 w/v % of the composition.

DETAILED DESCRIPTION OF THE INVENTION

Figure 1:
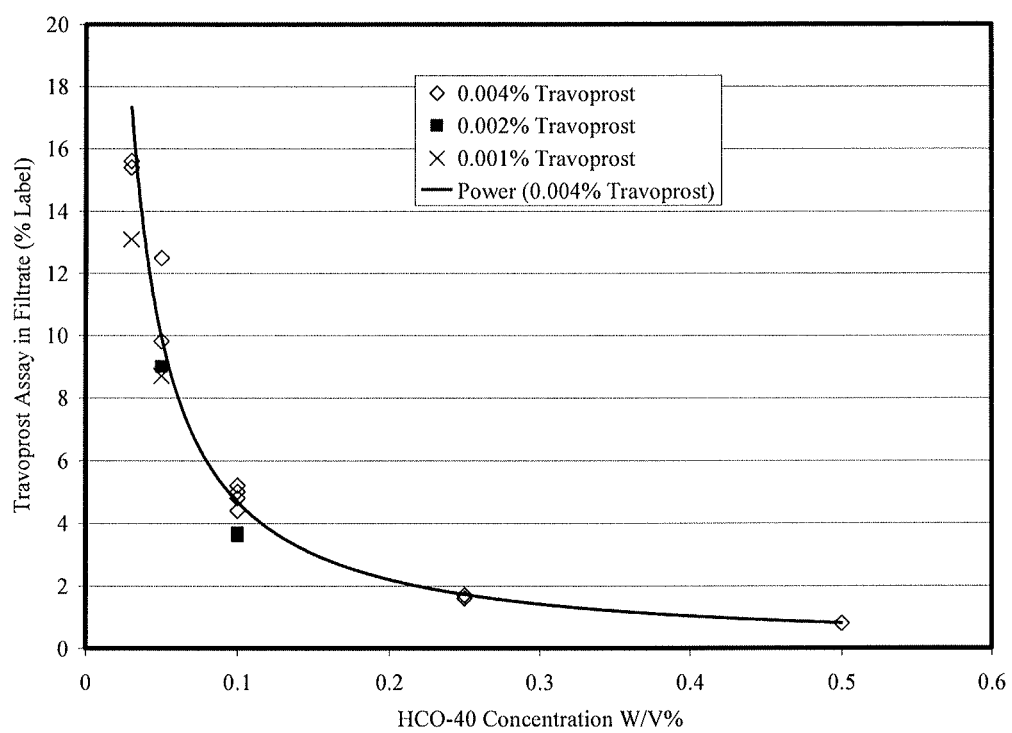
FIG. 1 is an exemplary graph of free therapeutic agent relative to surfactant concentration for an exemplary ophthalmic composition in accordance with an aspect of the present invention.

The present invention is predicated upon the provision of a pharmaceutical composition having a relatively low amount of surfactant and enhanced bioavailability of a therapeutic agent of the composition. The pharmaceutical composition is particularly desirable as a solution suitable for topical application to a biological target of the human body such as the ear, nose, throat or eye. In a highly preferred embodiment, the pharmaceutical composition is an aqueous or other type of ophthalmic composition that is provided as a solution. Moreover, it is preferred that the ophthalmic solution have a therapeutic agent suitable for treatment of one or more eye or ophthalmic maladies such as allergies, glaucoma, dry eye, macular degeneration, cataracts, combinations thereof or the like. As one highly preferred example, a therapeutic agent such as travoprost might be combined in an ophthalmic composition with a relatively low amount of surfactant for the treatment of glaucoma.

Unless otherwise indicated, percentages provided for the ingredients of the pharmaceutical composition of the present invention are weight/volume percentages (w/v %).

A combination of surfactant and therapeutic agent can be used according to the present invention to enhance the bioavailability of the therapeutic agent in the pharmaceutical composition. The combination of surfactant and therapeutic agent can be useful for various pharmaceutical compositions such as ophthalmic, otic, nasal and dermatological compositions, but has been found particularly useful for the ophthalmic compositions. Examples of compositions include: ophthalmic pharmaceutical compositions, such as topical compositions used in the treatment of glaucoma, infections, allergies or inflammation; compositions for treating contact lenses, such as cleaning products and products for enhancing the ocular comfort of patients wearing contact lenses; and various other types of ophthalmic compositions, such as ocular lubricating products, artificial tears, astringents, and so on. The compositions may be aqueous or non-aqueous, but will often be aqueous. As suggested, the compositions can be completely aqueous solutions, suspensions or otherwise.

The compositions of the present invention may contain various types of therapeutic agent. The invention can include therapeutic agents that are nonionic, anionic, cationic or combinations thereof. The therapeutic agent that exhibits higher bioavailability according to the present invention will typically be substantially or entirely non-ionic. The compositions of the present invention can also include one or more therapeutic agents where the bioavailability of those agents are not significantly affected by surfactant concentrations while the bioavailability of one or more other therapeutic agents are affected. For example, one of the former therapeutic agents could be part of a suspension while one of the latter therapeutic agents may be in the solution (e.g., dissolved in aqueous solution) of the suspension.

Examples of therapeutic agents that may be contained in the ophthalmic or other compositions of the present invention include timolol (e.g., timolol maleate), olopatadine (e.g., olopatadine hydrochloride), brinzolamide, tandospirone, roscovitine, nepafenac, combinations thereof or the like. Examples of therapeutic agents that may exhibit increased bioavailability in accordance with the present invention include, without limitation, hypotensive lipids (e.g., bimatoprost), and glucocorticoids (e.g., prednisolone, dexamethasone and lotoporednol). Therapeutic agents that typically exhibit significant increased bioavailability in accordance with the present invention are prostaglandins (e.g., latanoprost, travoprost and unoprostone).

As used herein, it is contemplated that the term "prostaglandin" includes, without limitation, natural prostaglandins, prostaglandin analogs, prostaglandin derivatives or any combination thereof.

The amount of therapeutic agent in the pharmaceutical composition will depend upon factors such as the efficacy of therapeutic agent at different concentrations, the compatibility of the therapeutic agent with other ingredients in the composition, the ability of biological target to accept various amounts of therapeutic agent, combinations thereof or the like. Generally speaking, the pharmaceutical composition can include at least 0.0001% by weight or w/v %, at least 0.001% by weight or w/v % or even at least 0.01% or 0.1% by weight or w/v % or more of the therapeutic agent. Also, generally speaking, the pharmaceutical composition can include less than 90% by weight or w/v %, less than 40% by weight or w/v % and still more typically less than 10% by weight or w/v % or less of the therapeutic agent.

Therapeutic agent that exhibits a desired degree of improved bioavailability according to the present invention is typically composed of agent that exhibits relatively low solubility in water. Thus, it is contemplated that the therapeutic agent of the pharmaceutical composition, particularly when it is employed in an aqueous ophthalmic composition, can exhibit solubility in water that is less than 0.1%, more typically less than 0.05%. It is also typically desirable for the therapeutic agent to be non-ionic, particularly in aqueous solution. It is also typically desirable for the therapeutic agent to be dissolved in solution of the ophthalmic or pharmaceutical composition which is typically accomplished with the assistance of the surfactant.

Further, therapeutic agent that exhibits a desired degree of improved bioavailability according to the present invention is typically lipophilic (i.e., it prefers an organic phase as compared to water or an aqueous phase). Such agent typically has a relatively high octanol/water partition coefficient. Thus, it is contemplated that the therapeutic agent of the pharmaceutical composition, particularly when it is employed in an aqueous ophthalmic composition, can exhibit an octanol/water partition coefficient that is typically at least 5 and more typically at least 10.

It is contemplated that the therapeutic agent can be partially or substantially entirely of one or more therapeutic agents that have the aforementioned solubility and/or partition component. As used herein, the term "substantially entirely", when used to describe what ingredient[s] are part of a component of the ophthalmic composition, means that it is contemplated that the component is formed entirely of one or more particular ingredient[s] or is formed substantially entirely of those one or more particular ingredient[s] with only a nominal amount (e.g., less than 5% or 1% by weight) of the component being formed of other than those one or more particular ingredients.

The surfactant included in the pharmaceutical composition of the present invention will often depend upon the therapeutic agent in the composition or other ingredients of the composition. Preferably, and particularly for aqueous applications, the surfactant can increase the solubility of the therapeutic agent and/or at least assist in assuring that the agent is distributed evenly in the composition. The surfactant may also promote the ability of the therapeutic agent to penetrate human tissue (e.g., corneal tissue of the eye) thereby further increasing the bioavailability of the agent.

The amount of surfactant will typically depend upon the therapeutic agent employed in the composition. The amount of surfactant employed is typically chosen so as to increase the bioavailability of the therapeutic agent. Generally speaking, the pharmaceutical composition can include at least 0.001% by weight or w/v %, at least 0.01% by weight or w/v %, at least 0.05% by weight or w/v % or even at least 0.5% or 1.0% by weight or w/v % or more of the surfactant. Also, generally speaking, the pharmaceutical composition can include less than 30% by weight or w/v %, less than 5% by weight or w/v %, still more typically less than 2% by weight or w/v % and even possibly less than 0.5% or 0.4% by weight or w/v % of the surfactant.

The surfactant can include non-ionic, an anionic, a cationic, or an amphoteric or zwitterionic surfactant or a combination of such surfactants. It is highly preferred that at least a portion or substantially the entirety of the surfactant be non-ionic for assisting in providing enhanced bioavailability of the therapeutic agent. As used herein, the phrase "substantially the entirety of the surfactant" is used to suggest either the entirety of the surfactant or the entirety of the surfactant with the exception of a nominal amount of surfactant or both.

Examples of potentially suitable surfactant include, without limitation, ethers of fatty alcohols and/or polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens™, polyoxyethylene stearates, combinations thereof or the like.

Surfactant that assists in providing for a desired degree of bioavailability according to the present invention is typically composed of agent that exhibits a relatively high hydrophile/lipophils/balance (HLB). Thus, it is contemplated that the surfactant of the pharmaceutical composition, particularly the ophthalmic composition, has an HLB value greater than 8, preferably greater than 10 and even possibly greater than 12.

The surfactant may include polysorbate 20 (TWEEN 20) (polyoxyethylene 20 sorbitan monolaurate), TWEEN 40, TWEEN 60, polysorbate 80 (TWEEN 80), Zwittergent 312, TEEPOL HB7, SPAN 85, pluronic or poloxamers, especially, PLURONIC L62LF, L101, and L64, F68, L44, L121, F-84 and P-103, PEG1000, and/or TETRONIC 1501, 150R1, 701, 901, 1301, and 130R1, poloxamer 333, poloxamer 334, and poloxamer 335, sorbitan oleate, polysorbate 81, polysorbate 85, polysorbate 120, sodium taurocholates, sodium deoxytaurocholates, chenodeoxycholic acid, ursodeoxycholic acid, or combinations thereof.

Preferably, the surfactant for the present invention is a non-ionic seed, nut and/or vegetable oil-derived surfactant. Particularly preferred are seed, nut and/or vegetable oils that have been hydrogenated, ethoxylated or both. Such surfactants include, but are not limited to babassu oil, almond oil, maize oil, palm kernel oil, castor oil, coconut oil, cotton seed oil, jojoba oil, linseed oil, mustard oil, olive oil, peanut oil, safflower oil sesame oil, soybean oil, sunflower-seed oil and wheat germ oil, their hydrogenated or ethoxylated derivatives or combinations thereof. Preferred oils are castor oil, babassu oil, almond oil, maize oil and palm kernel oil, most preferably castor oil and cababassu oil.

Particularly preferred surfactants include Polyoxyethylene (POE) (40) Hydrogenated castor oil (or PEG (40 Hydrogenated castor oil) (HCO-40), POE (60) Hydrogenated castor oil (HCO-60), and POE (200) Hydrogenated castor oil (HCO-200).

Without being bound by theory, it is believed that use of higher amounts or concentrations of surfactant relative to the therapeutic agent can results in higher amounts of the therapeutic agent being absorbed into the micelle of the surfactants as the therapeutic agent is solubilized. In turn, it is believed that such absorption can limit the amount of therapeutic agent readily available to a biological target (e.g., the cornea of a human eye) during topical application of the pharmaceutical composition (e.g., topical application of an ophthalmic solution). It should be understood that this theory is not binding upon the scope of the present invention unless otherwise specifically recited.

It is contemplated that the pharmaceutical composition of the present invention can include an effectively low amount of surfactant such that the concentration of the therapeutic agent located at a biological target is substantially greater than the concentration of therapeutic agent located at the same biological target after a separate application of a control composition. As used herein, a "separate application of a control composition" is an application of the control composition to a same biologic target of a separate animal. For example, testing can be performed on two sets of ten rabbits apiece wherein the composition of the present invention is applied to an eye of each rabbit of the first set while the control composition is applied to an eye of each rabbit of the second set. In such embodiment, the control composition is substantially identical to the pharmaceutical composition with the exception that the concentration of surfactant is at least doubled, more preferably tripled and even more typically quadrupled in the control composition relative to the pharmaceutical composition of the present invention. Moreover, the pharmaceutical composition of the present invention is applied in an amount that is equivalent to the amount of control composition applied.

Figure 2:
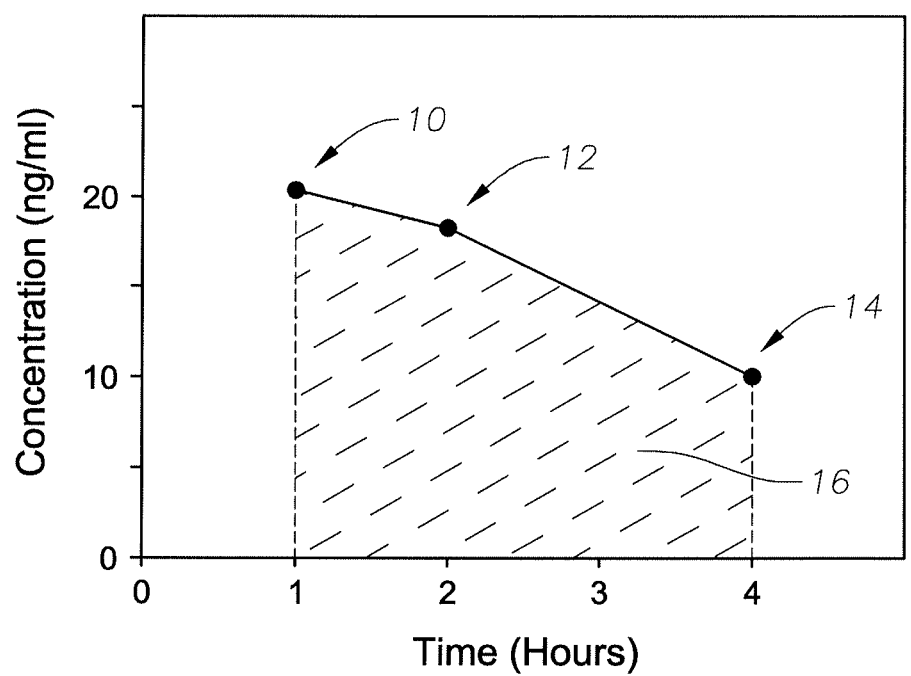
FIG. 2 is an exemplary graph of concentration of prostaglandin therapeutic agent at a biological target versus time.

For quantifying such concentrations, a graph is developed, an example of which is shown in FIG. 2, plotting concentration at the biological target relative to time after application of the pharmaceutical composition. The concentration is determined at three separate times at the biological target. In particular, the concentration is determined at 1 hour, 2 hours and 4 hours after application. These points are then plotted on the graph. Examples of such points 10, 12, 14 are shown in FIG. 2. Those points can then be connected by line segments and the area 16 under those line segments (referred to herein as area under the concentration/time curve) is determined as a quantification of concentration. Using this area under the curve measurement, it has been determined that the area under the concentration/time curve when determined for the pharmaceutical composition of the present invention as applied to the biological target is at least 130%, more typically at least 150% and even possibly at least 200% relative to the area under the concentration/time curve when determined for the control composition as applied to the biological target. One preferred protocol for application of control composition and pharmaceutical composition as well as measurement of concentration of therapeutic agent is provided in the example section below.

As an example of area under the curve measurements, an exemplary situation is provided wherein the concentrations at 1, 2 and 4 hours for the composition of the present invention is 20 nanograms per milliliter (ng/ml) and the concentrations at 1, 2 and 4 hours for the control composition are 10 ng/ml. In such a situation the area under the curve for the composition of the present invention is 20 ng/ml×3 hr, which is 60 while the area under curve for the control composition is 10 ng/ml×3 hr, which is 30. In this scenario, the area under the curve for the composition of the present invention is 200% that of the area under the curve for the composition of the control composition.

It has been found that the bioavailability of certain therapeutic agents is sensitive to the amount of surfactant employed in conjunction with those therapeutic agents. This is particularly true when the pharmaceutical composition of the present invention is an ophthalmic composition such as a single-dose or multi-dose aqueous ophthalmic composition. As a class, it is believed that the therapeutic agent classified herein as prostaglandins exhibit a higher degree of bioavailability when employed in conjunction with relatively low concentrations of surfactants classified herein as vegetable, nut or seed oil surfactants, particularly vegetable oil surfactants. It has been discovered that travoprost in particular exhibits a higher degree of bioavailability in an aqueous ophthalmic composition of the present invention when used in conjunction with a relatively low concentration of an ethoxylated and/or hydrogenated vegetable oil surfactant such as Polyoxyethylene (POE) (40) Hydrogenated castor oil (or PEG (40 Hydrogenated castor oil) (HCO-40), POE (60) Hydrogenated castor oil (HCO-60), and POE (200) Hydrogenated castor oil (HCO-200), combinations thereof or the like. As such, it is contemplated that the surfactant of the present invention can be entirely or substantially entirely one or more ethoxylated and/or hydrogenated vegetable oils such as Polyoxyethylene (POE) (40) Hydrogenated castor oil (or PEG (40 Hydrogenated castor oil) (HCO-40), POE (60) Hydrogenated castor oil (HCO-60), and POE (200) Hydrogenated castor oil (HCO-200), combinations thereof or the like and the therapeutic agent can be entirely or substantially entirely one or more prostaglandins such as latanoprost, travoprost, unoprostone or combinations thereof.

In such an aqueous ophthalmic composition having prostaglandin therapeutic agent (e.g., travoprost) and hydrogenated and/or ethoxylated vegetable oil surfactant (e.g., HCO-40), the amount of such therapeutic agent is typically at least 0.00001 w/v %, at least 0.0001% w/v % or even at least 0.001 w/v % of the composition. Moreover, such composition typically includes less than 5 w/v %, more typically less than 0.05% w/v % and still more typically less than 0.01 w/v % such therapeutic agent. Further, the composition typically includes at least 0.005 w/v %, at least 0.01 w/v % or even at least 0.03 w/v % such surfactant. The composition also typically includes less than 0.5 w/v %, more typically less than 0.4 w/v %, even more typically less than 0.3 w/v % and even possibly less than 0.15 w/v % such surfactant.

It is contemplated that area under the concentration/time curve measurements as described above can specifically be performed for such prostaglandin/surfactant combinations. The ophthalmic composition having prostaglandin therapeutic agent and hydrogenated and/or ethoxylated vegetable oil surfactant preferably includes an effectively low amount of surfactant such that the area under the concentration/time curve when determined for the ophthalmic composition of the present invention as for the aqueous humor of an eye is at least 130%, more typically at least 150% and even possibly at least 200% relative to the area under the concentration/time curve when determined for the control composition as for the aqueous humor of an eye. In such embodiment, the control composition is substantially identical to the pharmaceutical composition with the exception that the concentration of surfactant is at least doubled, more preferably tripled and even more typically quadrupled in the control composition relative to the ophthalmic composition of the present invention. Moreover, the ophthalmic composition of the present invention is applied in an amount that is equivalent to the amount of control composition applied. It is further contemplated that such concentrations can be similarly taken for the iris-ciliary body.

As suggested previously, concentrations for the composition of the present invention and the control composition can be carried out, for at least one embodiment of the present invention, according to the testing protocol provided below.

The pharmaceutical compositions of the present invention, particularly when they are ophthalmic compositions, will generally be formulated as sterile aqueous solutions. These compositions are also formulated so as to be compatible with the eye and/or other tissues to be treated with the compositions. The ophthalmic compositions intended for direct application to the eye will typically be formulated so as to have a pH and tonicity that are compatible with the eye. It is also contemplated that the compositions can be suspensions or other types of solutions. The ophthalmic compositions will typically have a pH in the range of 4 to 9, preferably 5.5 to 8.5, and most preferably 5.5 to 8.0. Particularly desired pH ranges are 6.0 to 7.8 and more specifically 6.4 to 7.2 or 7.5.

The pharmaceutical compositions, particularly ophthalmic compositions, of the present invention can include a polymer or a viscosity agent that further enhances bioavailability by extending the retention time of the compositions in or on the tear film of the eye, the cull-de-sac of the eye or elsewhere on the eye or another biological target. The preferred polymers include, without limitation, hydroxyethyl cellulose, hydroxypropylmethyl cellulose, carobomer, carbopol, xanthan gum, any combination thereof or the like.

In one embodiment, the pharmaceutical composition of the present invention is an ophthalmic aqueous solution or other similar solution. Such a solution will typically include a preservative system. As used herein, a "preservative system" is one or a group of ingredients included within the ophthalmic solution for maintaining antimicrobial activity in the solution. A solution may be a self-preserving solution if its ingredients naturally provide for anti-microbial activity and such solution still includes a preservative system. Examples of ophthalmic solutions or ingredients suitable for such solutions where those solutions may benefit from the teaching of the present invention are disclosed in U.S. Pat. Nos. 3,931,319; 4,027,020; 4,407,791; 4,525,346; 4,836,986; 5,037,647; 5,300,287; 5,817,277; 6,503,497; 5,741,817; 6,319,464; 6,348,190; 6,348,190; 6,482,799; 5,320,843; 5,221,664; 6,034,043; 4,522,806; 6,017,861 and U.S. Patent Publications: 2002/0122831; and PCT application WO 91/09523 (Dziabo et al.); and JP 2003-104870, all of which are incorporated herein by reference for all purposes. One particular Ophthalmic Solution which may benefit from the teachings of the present invention is disclosed in U.S. patent application Ser. No. 12/396,680, titled "Aqueous Pharmaceutical Compositions Containing Borate-Polyol Complexes", filed on the same date as the present invention and incorporated herein by reference for all purposes.

Accordingly, the preservative system of the pharmaceutical composition of the present invention can include a borate. As used herein, the term "borate" shall refer to boric acid, salts of boric acid and other pharmaceutically acceptable borates, or combinations thereof. Most suitable are: boric acid, sodium borate, potassium borate, calcium borate, magnesium borate, manganese borate, and other such borate salts. Borate interacts with polyols, such as glycerol, propylene glycol, sorbitol and mannitol, to form borate polyol complexes. The type and ratio of such complexes depends on the number of OH groups of a polyol on adjacent carbon atoms that are not in trans configuration relative to each other. It shall be understood that weight/volume percentages of the ingredients polyol and borate include those amounts whether as part of a complex or not.

When used, borate is generally used in the composition of the present invention in an amount that is greater than about 0.001 w/v %, more typically greater than about 0.01 w/v % and even more typically greater than about 0.07% w/v % of the pharmaceutical composition. Moreover, when used, the borate is generally used in the compositions of the present invention in an amount that is less than about 5 w/v %, more typically less than about 1.2 w/v % and even more typically less than about 0.8 w/v % of the pharmaceutical composition.

The preservative system of the pharmaceutical composition may also include one or more polyols. As used herein, the term "polyol" includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. Preferred polyols are sugars, sugar alcohols and sugar acids, including, but not limited to: mannitol, glycerin, xylitol, sorbitol and propylene glycol.

When used, polyol generally used in the composition of the present invention in an amount that is greater than about 0.001 w/v %, more typically greater than about 0.01 w/v % and even more typically greater than about 0.07 w/v % of the pharmaceutical composition. Moreover, when used, polyol is generally used in the compositions of the present invention in an amount that is less than about 5 w/v %, more typically less than about 1.2 w/v % and even more typically less than about 0.8 w/v % of the pharmaceutical composition.

The compositions of the present invention can include a preservative. Potential preservatives include, without limitation, hydrogen peroxide, chlorine containing preservatives such as benzalkonium chloride or others. According to a preferred aspect, however, the ophthalmic composition of the present invention is substantially free of any chloride containing preservatives and, particularly, is substantially free of benzalkonium chloride. Highly preferred preservatives included for ophthalmic uses are polymeric quaternary ammonium compounds. It is noted that use of the amounts of surfactant specified herein can increase bioavailability in a manner that can at least partially or substantially entirely offset losses in bioavailability that may occur when benzalkonium chloride or other such ingredient are not present.

As used herein, the phrase "substantially free of" as it refers to an ingredient of the ophthalmic composition means that the ophthalmic solution is either entirely devoid of that particular ingredient or includes only a nominal amount of that particular ingredient.

The polymeric quaternary ammonium compounds useful in the compositions of the present invention are those which have an antimicrobial effect and which are ophthalmically acceptable. Preferred compounds of this type are described in U.S. Pat. Nos. 3,931,319; 4,027,020; 4,407,791; 4,525,346; 4,836,986; 5,037,647 and 5,300,287; and PCT application WO 91/09523 (Dziabo et al.). The most preferred polymeric ammonium compound is polyquaternium 1, otherwise known as POLYQUAD® or ONAMERM® with a number average molecular weight between 2,000 to 30,000. Preferably, the number average molecular weight is between 3,000 to 14,000.

When used, the polymeric quaternary ammonium compounds or other preservatives are generally used in the compositions of the present invention in an amount that is greater than about 0.00001 w/v %, more typically greater than about 0.0003 w/v % and even more typically greater than about 0.0007 w/v % of the pharmaceutical composition. Moreover, when used, the polymeric quaternary ammonium compounds or other preservatives are generally used in the compositions of the present invention in an amount that is less than about 3 w/v %, more typically less than about 0.003 w/v % and even more typically less than about 0.0015 w/v % of the pharmaceutical composition.

The pharmaceutical compositions of the present invention can be a multi-dose ophthalmic compositions having sufficient antimicrobial activity to allow the composition to satisfy the USP preservative efficacy requirements, as well as other preservative efficacy standards for aqueous pharmaceutical compositions.

The preservative efficacy standards for multi-dose ophthalmic solutions in the U.S. and other countries/regions are set forth in the following table:

Preservative Efficacy Test ("PET") Criteria (Log Order Reduction of Microbial Inoculum Over Time

|  | Bacteria | Fungi |
| --- | --- | --- |
| USP 27 | A reduction of 1 log (90%), by day 7; 3 logs (99.9%) by day 14; and no increase after day 14 | The compositions must demonstrate over the entire test period, which means no increases of 0.5 logs or greater, relative to the initial inoculum |
| Japan | 3 logs by 14 days; and no increase from day 14 through day 28 | No increase from initial count at 14 and 28 days |
| Ph. Eur. A[1] | A reduction of 2 logs (99%) by 6 hours; 3 logs by 24 hours; and no recovery after 28 days | A reduction of 2 logs (99%) by 7 days, and no increase thereafter |
| Ph. Eur. B | A reduction of 1 log at 24 hours; 3 logs by day 7; and no increase thereafter | A reduction of 1 log (90%) by day 14, and no increase thereafter |
| FDA/ISO 14730 | A reduction of 3 logs from initial challenge at day 14; and a reduction of 3 logs from rechallenge | No increase higher than the initial value at day 14, and no increase higher than the day 14 rechallenge count through day 28 |

[1] There are two preservative efficacy standards in the European Pharmacopoeia "A" and "B".

The standards identified above for the USP 27 are substantially identical to the requirements set forth in prior editions of the USP, particularly USP 24, USP 25 and USP 26.

Table A below provides a listing of exemplary ingredients suitable for an exemplary preferred formulation of the ophthalmic composition of the present invention and a desired percentage for those ingredients.

TABLE A

| Ingredient | w/v Percent |
| --- | --- |
| Travoprost | 0.004 |
| Polyoxyl 40 Hydrogenated Castor Oil (HCO-40) | ≤0.2 or ≥0.05 |
| Boric Acid | 0.3 |
| Zinc Chloride | 0.0025 |
| Sorbitol | 0.25 |
| Propylene Glycol | 1.6 |
| Sodium Chloride | 0.35 |
| NaOH | sufficient to achieve pH = 6.8 |
| purified water | Q.S. 100 |

It is understood that the weight/volume percents in table A can be varied by ±10%, ±20%, ±30%, ±90% of those weight/volume percents or more and that those variances can be specifically used to create ranges for the ingredients of the present invention. For example, an ingredient weight/volume percent of 10% with a variance of ±20% means that the ingredient can have a weight/volume percentage range of 8% to 12 w/v %.

With reference to FIG. 1, experiments were performed for several pharmaceutical compositions varying the amount of surfactant in those compositions. In particular, the amount or percentage of free or available travoprost was determined for compositions having the same ingredients as the compositions of table E with the exception that surfactant level were varied. As can be seen, the concentration of surfactant can have a significant effect upon the availability of the travoprost.

Notably, these preservative systems can at least assist in providing stability to the compositions of the present invention. Such systems can, in many instances, offset stability that may be lost through the use of less surfactant.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As suggested above, the relatively low concentrations of surfactant can be employed in formulations having multiple different therapeutic agents for producing desired bioavailability of those agents. Additionally, however, it has been found, that composition with particular combinations of therapeutic (combination compositions) agents gain significant benefits from the surfactant of the present invention, particularly when it is used at lower concentrations, but also potentially when it is used at higher concentrations.

In particular, it has been found that the surfactant that, when used at low concentrations, assists in solubilizing and/or increases bioavailability of the particular therapeutic agents discussed herein (e.g., prostaglandins such as travoprost) and can also act as a wetting agent for other therapeutic agents such a carbonic anhydrase inhibitors such as brinzolamide. Thus, the surfactant can provide a dual function within the composition (e.g., ophthalmic aqueous composition). This dual function can then allow the composition to include only a single surfactant. Of course, multiple surfactants may be employed unless otherwise specifically stated.

It is contemplated that any of the preferred surfactants discussed herein as being capable of enhancing the bioavailability of a therapeutic agent and/or having the properties that provide such capability may used to perform this dual function. Thus, a preferred surfactant for combination composition, like the preferred surfactant for the rest of the compositions herein, is a non-ionic seed, nut and/or vegetable oil-derived surfactant. Particularly preferred are seed, nut and/or vegetable oils that have been hydrogenated, ethoxylated or both. Such surfactants include, but are not limited, to babassu oil, almond oil, maize oil, palm kernel oil, castor oil, coconut oil, cotton seed oil, jojoba oil, linseed oil, mustard oil, olive oil, peanut oil, safflower oil sesame oil, soybean oil, sunflower-seed oil and wheat germ oil, their hydrogenated or ethoxylated derivatives or combinations thereof. Preferred oils are castor oil, babassu oil, almond oil, maize oil and palm kernel oil, most preferably castor oil and cabaassu oil.

Particularly preferred surfactants include Polyoxyethylene (POE) (40) Hydrogenated castor oil (or PEG (40 Hydrogenated castor oil) (HCO-40), POE (60) Hydrogenated castor oil (HCO-60), and POE (200) Hydrogenated castor oil (HCO-200).

Where higher bioavailability is desired, the surfactant for the combination composition can be used at the low concentrations that have already been disclosed herein. However, it is also contemplated that higher concentrations of such surfactant may be employed in circumstances where bioavailability is of less concern.

The combination composition benefits from particular advantages when it is formulated as a suspension. The use of the surfactant as discussed for the combination composition can allow for substantially complete (i.e., at least 80 or 90%) or complete solubilization of one therapeutic agent (e.g., a prostaglandin such as travoprost). At the same time, the surfactant can provide wetting and/or stabilization to the other therapeutic agent (e.g., a carbonic anhydrase inhibitor such as brinzolamide) which is suspended within the suspension. When the surfactant is used at the low concentrations discussed herein, it can also significantly improve the bioavailability of the non-suspended agent. Further, the preferred surfactant can often prevent the solubilized therapeutic agent from binding to container walls as would be seen if other surfactants were employed.

It is to be understood that any of the excipients discussed herein can be used in these combination compositions whether the compositions are suspensions, other aqueous solutions or other compositions. Moreover, the skilled artisan will understand that the discussions of the therapeutic agents and surfactants, when discussing any of the compositions herein, also applies to the combination compositions.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

COMPARATIVE EXAMPLES

Table B below provides two compositions, which include a preferred ophthalmic composition of the present invention as well as a control composition. The control composition has a surfactant level higher than the preferred composition according to the parameters discussed above.

TABLE B

| INGREDIENTS | CONTROL | PREFERRED COMPOSITION |
|---|---|---|
| Travoprost | 0.004 | 0.004 |
| Polyoxyethylene 40 Hydrogenated Castor Oil (HCO-40) | 0.5 | 0.1 |
| Boric Acid | 0.3 | 0.3 |
| Zinc Chloride | 0.0025 | 0.0025 |
| Sorbitol | 0.25 | 0.25 |
| Propylene Glycol | 1.6 | 1.6 |
| Sodium Hydroxide and/or Hydrochloric Acid | Adjust pH 6.0 | Adjust pH 6.0 |
| Purified Water | QS 100 w/v % | QS 100 w/v % |

The amount of surfactant (i.e., HCO-40) in the control composition is 5 times the amount of surfactant in the preferred composition. The preferred composition was applied to the eyes of a first set of rabbits and then a separate application of the control composition was applied to the eyes of a second set of rabbits. After application of the preferred composition and after application of the control composition, concentrations in nanograms per milliliter (ng/mL) of therapeutic agent (i.e., travoprost free acid) were determined for the Aqueous Humor and the Iris Ciliary of the eyes at various times. The results are respectively shown below in TABLE C and TABLE D.

TABLE C

| Time | Control | Standard Deviation | Preferred Composition | Standard Deviation |
|---|---|---|---|---|
| 0.25 | 1.13 | 0.37 | 2.01 | 0.87 |
| 0.5 | 3.82 | 1.31 | 9.17 | 2.72 |
| 1 | 6.87 | 2.40 | 20.78 | 4.35 |
| 2 | 5.90 | 1.17 | 18.40 | 6.08 |
| 4 | 5.05 | 2.78 | 10.24 | 3.69 |
| 6 | 0.57 | 0.15 | 1.20 | 0.77 |

TABLE D

| Time | Control | Standard Deviation | Preferred Composition | Standard Deviation |
|---|---|---|---|---|
| 0.25 | 1.40 | 0.29 | 1.71 | 0.42 |
| 0.5 | 2.43 | 0.94 | 5.86 | 1.88 |
| 1 | 3.33 | 0.76 | 9.32 | 2.68 |
| 2 | 2.79 | 0.39 | 7.59 | 3.25 |
| 4 | 1.98 | 1.14 | 4.69 | 1.59 |
| 6 | BLQ | — | 0.75 | 0.26 |

As can be seen from Tables B through D, the amount of therapeutic agent in the tested portion of the eyes was substantially higher in the preferred composition relative to the control composition.

Table E below shows further preferred compositions A, B and C of the present invention. After application of these preferred compositions in the eyes of rabbits, concentrations (in nanograms per milliliter (ng/mL) of therapeutic agent is (i.e., travoprost free acid) were determined for the Aqueous Humor of the eyes at various times.

TABLE E

| Ingredients | Composition A | Composition B | Composition C |
|---|---|---|---|
| Travoprost | 0.004 | 0.004 | 0.002 |
| Polyoxyethylene 40 Hydrogenated Castor Oil (HCO-40) | 0.1 | 0.03 | 0.1 |
| Boric Acid | 0.3 | 0.3 | 0.3 |
| Mannitol | 0.3 | 0.3 | 0.3 |
| Propylene Glycol | 0.75 | 0.75 | 0.75 |
| Sodium chloride | 0.35 | 0.35 | 0.35 |
| Polyquaternium-1 | 0.001 | 0.001 | 0.001 |
| Hydrochloric Acid and/or Sodium HCl | Adj pH to 6.8 | Adj pH to 6.8 | Adj pH to 6.8 |
| Purified Water | QS to 100% | QS to 100% | QS to 100% |

Table F below shows the concentrations in nanograms per milliliter (ng/mL) of the therapeutic agent of compositions A, B and C in the Aqueous humor of eyes of rabbits at various times after the application of the compositions.

TABLE F

| Sampling Time (n) | Composition A | Composition B | Composition C |
|---|---|---|---|
| 60 minutes (9-10) | 22.79 ± 7.62 | 25.64 ± 9.34 | 13.21 ± 7.79 |
| 120 minutes (10) | 15.46 ± 6.73 | 23.86 ± 4.67 | 9.23 ± 4.02 |
| 240 minutes (10) | 4.73 ± 1.23 | 12.68 ± 9.81 | 2.59 ± 1.46 |

As can be seen, concentrations of the therapeutic agent from Compositions A through C in the Aqueous humor of the rabbits are desirably high.

Table G below shows a further preferred composition D of the present invention.

TABLE G

| INGREDIENT | COMPOSITION D |
|---|---|
| Travoprost | 0.004 |
| Timolol Maleate | 0.68 |
| Polyoxyl 40 Hydrogenated Castor Oil (HCO-40) | 0.1 |
| Boric Acid | 0.3 |
| Mannitol | 0.3 |
| Propylene Glycol | 0.75 |
| Sodium Chloride | 0.25 |
| Polyquaternium-1 | 0.001 |
| Sodium Hydroxide | Adj. pH 6.8 |
| Hydrochloric Acid | Adj. pH 6.8 |
| Purified Water | QS 100% |

As discussed above, the amount of surfactant can affect the stability of the compositions. Table H shows results of stability testing of composition B through E relative to Composition A, which has a higher surfactant concentration. All formulations A through E were formulated like the compositions of table E and contained 0.3% boric acid, 0.3% mannitol, 0.001% Polyquaternium-1 and were adjusted to pH 6.8 with sodium hydroxide and or hydrochloric acid. Composition A and composition each contained 0.66% sodium chloride while compositions C through D included 0.75% propylene glycol and 0.35% sodium chloride instead.

Each of the compositions A-E was packaged utilizing a syndiotactic polypropylene container, polypropylene plug and a polypropylene cap. They were stored at a stress condition of 55° C. for 8 weeks. Control samples were stored in a refrigerator at 4° C. These samples were analyzed for travoprost assay and the travoprost degradation product (travoprost free acid). The results are provided in Table. The formulations loose about 6 to 8% moisture upon 8 weeks storage at 55° C. As a result they show increase in travoprost assay at 8 weeks 55° C.

(i.e., fraction travoprost outside the HCO-40 micelle), can be obtained by filtering the solution through a 3000 molecular weight cut off filter.

The following procedure was used to determine the free fraction of travoprost. About 2 ml of formulation was placed in a centrifuge tube fitted with a 3000 Molecular weight cut off regenerated cellulose filter. The sample was centrifuged for approximately 90 minutes at 2000 r.p.m. to pass approxi-

TABLE H

| | Travoprost Concentration w/v % | HC0-40 Concentration w/v % | Travoprost Assay at 4 C. (% Label) | Travoprost Assay at 8 Wks/ 55 C. (% Label) | Travoprost free acid Assay at 4 C. (% of Travoprost) | Travoprost free acid (% of Travoprost) |
|---|---|---|---|---|---|---|
| A | 0.004 | 0.5 | 96 | 102 | 0.0 | 0.7 |
|   |       |     | 96 | 101 | 0.0 | 0.7 |
| B | 0.004 | 0.1 | 99 | 104 | 0.0 | 2.4 |
|   |       |     | 99 | 103 | 0.0 | 2.4 |
| C | 0.004 | 0.1 | 97 | 101 | NT  | 2.7 |
|   |       |     | 97 | 102 |     | 2.7 |
| D | 0.004 | 0.05 | 93 | 100 | 0.3 | 3.1 |
|   |       |      | 95 | 100 | 0.3 | 3.1 |
| E | 0.004 | 0.03 | 91 | 93  | 0.0 | 3.4 |
|   |       |      | 92 | 96  | 0.0 | 3.4 |

As can be seen, the amount of the degradation product increases with decreasing HCO-40 concentration. However, such increase is relatively insignificant for the overall compositions since the amount of degradation product is still quite small compare to the total amount of travoprost that remains in solution.

Bioavailability Examples

Polyoxyl hydrogenated castor oil 40 (HCO-40) is a surfactant that solubilizes travoprost and incorporates travoprost into its micelles. HCO-40 can be obtained by reacting 40 to 45 moles of ethylene oxide with 1 mole of hydrogenated castor oil. Thus, it typically has a high enough molecular weight such that it will not be filtered through a 3000 molecular weight cut off filter. An estimate of free fraction of travoprost, mately 1 to 1.2 mL of formulation through the filter. The filtrate and retentate were then collected and assayed for travoprost using a HPLC procedure. The results are provided in Table I below. Note that the compositions 1 through 15 are all formulated like those in Table E and each composition contains 0.3% boric acid, 0.3% mannitol, 0.001% Polyquaternium-1 and were adjusted to pH 6.8 with sodium hydroxide and/or hydrochloric acid.

The assay values of filtrate represent the free fraction of travoprost. The results show that free fraction of travoprost increases with decreasing HCO-40 concentration. It is desired to have free fraction of travoprost greater than 1%, preferably greater than 2% and most preferably greater than 4%. The topical ocular bioavailability is expected to increase with increasing travoprost concentration and free fraction of travoprost.

TABLE I

| # | Other Excipients | Travoprost Concentration | HCO-40 Concentration | Travoprost Assay of Filtrate, % Label | Travoprost Assay of Retentate, % Label | Weight of Filtrate | Weight of Retentate |
|---|---|---|---|---|---|---|---|
| 1 | 0.66% NaCl | 0.004 | 0.5 | 0.8 | 176 | 1.00 | 1.00 |
| 2 | 0.66% NaCl | 0.004 | 0.25 | 1.7 | 188 | 1.01 | 0.99 |
| 3 | 0.66% NaCl | 0.004 | 0.25 | 1.6 | 210 | 1.12 | 0.86 |
| 4 | 0.66% NaCl | 0.002 | 0.1 | 3.6 | 222 | 1.19 | 0.80 |
| 5 | 0.75% propylene glycol,, 0.35% NaCl | 0.002 | 0.1 | 3.7 | 199 | 1.11 | 0.89 |
| 6 | 0.75% propylene glycol,, 0.35% NaCl | 0.004 | 0.1 | 5.2 | 226 | 1.18 | 0.81 |
| 7 | 0.75% propylene glycol,, 0.35% NaCl | 0.004 | 0.1 | 4.8 | 197 | 1.00 | 0.99 |
| 8 | 0.75% propylene glycol,, 0.35% NaCl | 0.004 | 0.1 | 5.0 | 205 | 1.13 | 0.88 |
| 9 | 0.66% NaCl | 0.004 | 0.1 | 4.4 | 216 | 1.13 | 0.87 |
| 10 | 0.75% propylene glycol,, 0.35% NaCl | 0.001 | 0.05 | 8.7 | 187 | 1.03 | 0.99 |
| 11 | 0.75% propylene glycol,, 0.35% NaCl | 0.002 | 0.05 | 9.0 | 214 | 1.18 | 0.81 |
| 12 | 0.75% propylene glycol,, 0.35% NaCl | 0.004 | 0.05 | 9.8 | 196 | 1.14 | 0.85 |
| 13 | 0.75% propylene glycol,, 0.35% NaCl | 0.004 | 0.05 | 12.5 | 217 | 1.25 | 0.76 |

TABLE I-continued

| # | Other Excipients | Travoprost Concentration | HCO-40 Concentration | Travoprost Assay of Filtrate, % Label | Travoprost Assay of Retentate, % Label | Weight of Filtrate | Weight of Retentate |
|---|---|---|---|---|---|---|---|
| 14 | 0.75% propylene glycol,, 0.35% NaCl | 0.001 | 0.03 | 13.1 | 219 | 1.28 | 0.73 |
| 15 | 0.75% propylene glycol,, 0.35% NaCl | 0.004 | 0.03 | 15.6 | 166 | 1.15 | 0.86 |
| 16 | 0.75% propylene glycol,, 0.35% NaCl | 0.004 | 0.03 | 15.4 | 201 | 1.26 | 0.75 |

Thus, in general for the present invention, half (1 ml) of a volumetric amount (2 ml) of composition of the present invention is forced through a molecular weight cut-off filter to form half of the composition into a filtrate and half into a retentate. For such composition, it is typically desirable for the concentration of surfactant in the composition to be such that the concentration of therapeutic agent is relatively high in the filtrate. This can be quantified as a filtrate/retentate ratio, which is equal to the weight/volume concentration of therapeutic agent in the filtrate divided by the weight/volume concentration of therapeutic agent in the retentate. This ratio for the present invention is determined when half (1 ml) of an amount (2 ml) of composition of the present invention is forced through a molecular weight cut-off filter to form a filtrate and a retentate where the molecular weight cut-off filter does not allow any or any substantial is portion of the surfactant to flow through the weight cut-off filter. For the present invention, this ratio is typically greater than 0.0060, more typically greater than 0.014 and even possibly greater than 0.035.

Concentration Testing Protocol

The following protocol is at least one method of determining concentration of therapeutic agent at a biologic target. New Zealand white rabbits each receive a single 30 µl topical ocular dose to each eye. Aqueous humor samples are collected immediately after euthanasia at the time points provided in results Table C. The concentration of travoprost free acid is then determined using tandem mass spectrometry (LC-MS/MS) analysis. Travoprost free acid is extracted from the aqueous humor samples and reconstituted in a water ethanol mixture. LC-MS-MS analysis for the determination of travoprost free acid concentrations is carried out using a Perkin Elmer Sciex AP 3, atmospheric pressure ionization mass spectrometer with an electrospray inlet and turbo ion spray, in the negative ion mode. Phenomenex ODS C18 (2) HPLC column is used. 5 mM ammonium formate buffer pH 6.3: methanol (30:70) is used as mobile phase.

COMBINATION COMPOSITION EXAMPLES

Table J below provides two exemplary preferred formulations (formulations R and S) of combination compositions, which are aqueous suspensions. The suspensions include two therapeutic agents, the carbonic anhydrase inhibitor brinzolamide and the prostaglandin travoprost. The compositions also include low concentrations of an exemplary preferred surfactant, HCO-40.

TABLE J

| Composition W/V | Composition R | Composition S |
|---|---|---|
| Brinzolamide | 1.0 g | 1.0 g |
| Travoprost | 0.0015 g | 0.004 g |
| HCO-40 | 0.2 g | 0.2 g |
| Carbomer 974 P | 0.4 g | 0.4 g |
| Mannitol | 3.5 g | 2.6 g |
| Edetate disodium | 0.01 g | 0.01 g |
| Benzalkonium Chloride | 0.01 g | 0.015 g |
| Sodium chloride | 0.18 g | 0.35 g |
| NaOH/HCl | q.s. to 6.5 | q.s. to 6.5 |
| Purified water | q.s. 100 ml | q.s. 100 ml |

For purposes of comparison, table K below provides two formulations (formulations T and U) of combination compositions, which are also aqueous suspensions. The suspensions include two therapeutic agents, the carbonic anhydrase inhibitor brinzolamide and the prostaglandin travoprost. The compositions also include relatively higher concentrations of the surfactant HCO-40 and include tyloxapol as an additional surfactant.

TABLE K

| Composition W/V | Composition T | Composition U |
|---|---|---|
| Brinzolamide | 1.0 g + 3% excess | 1.0 g + 3% excess |
| Tyloxapol | 0.025 g | 0.025 g |
| Travoprost | 0.0015 g | 0.004 g |
| HCO-40 | 0.5 g | 0.5 g |
| Carbomer 974 P | 0.4 g | 0.4 g |
| Povidone K29-32 | 0.2 g | 0.2 g |
| Mannitol | 3.5 g | 2.6 g |
| Edetate disodium | 0.01 g | 0.01 g |
| Benzalkonium Chloride | 0.01 g | 0.015 g |
| Sodium chloride | 0.18 g | 0.35 g |
| NaOH/HCl | q.s. to 6.5 | q.s. to 6.5 |
| Purified water | q.s. 100 ml | q.s. 100 ml |

Figure 3:
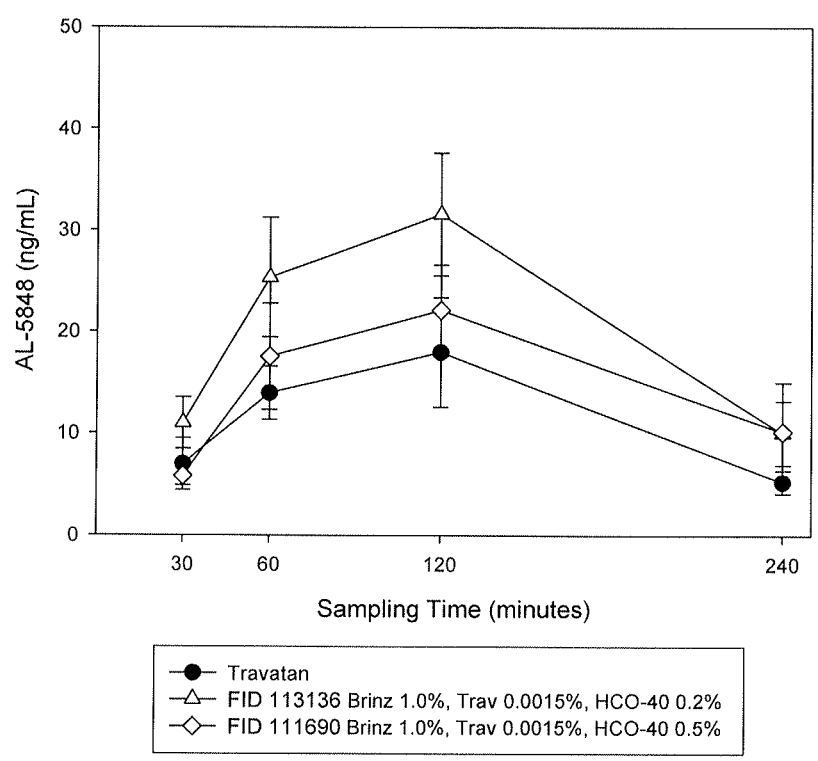
FIG. 3 is an exemplary graph of concentration of prostaglandin therapeutic agent at a biological target versus time in accordance with an aspect of the present invention.
Figure 4:
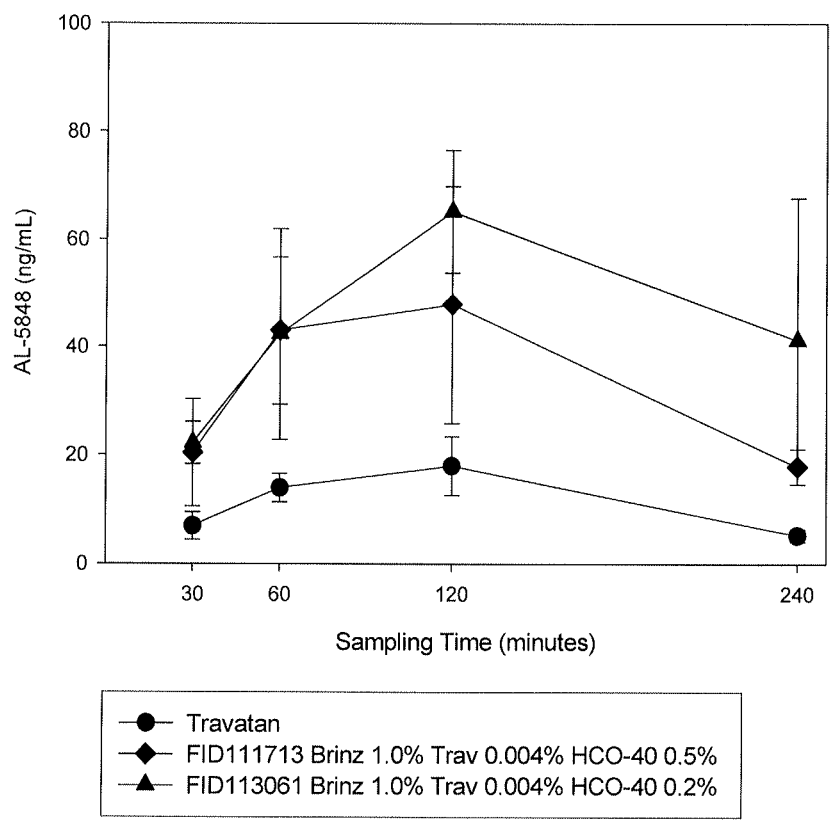
FIG. 4. is an exemplary graph of concentration of prostaglandin therapeutic agent at a biological target versus time in accordance with an aspect of the present invention.
Figure 5:
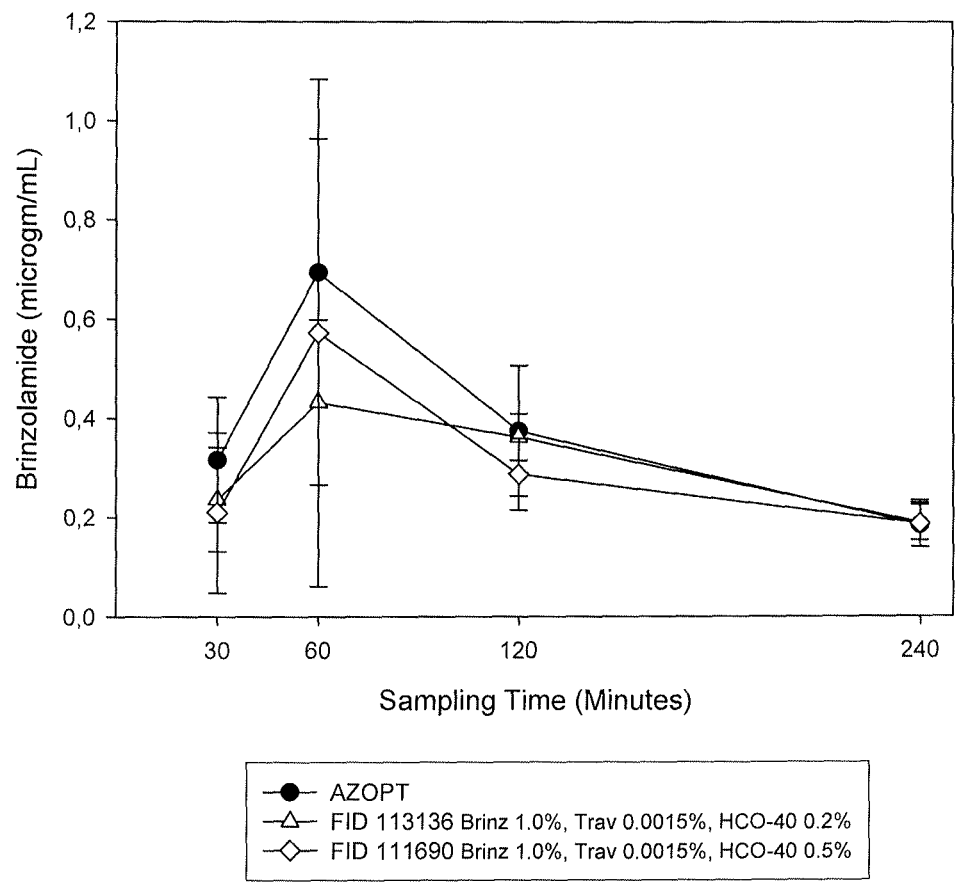
FIG. 5. is an exemplary graph of concentration of therapeutic agent (i.e., carbonic anhydrase inhibitor) at a biological target versus time in accordance with an aspect of the present invention.
Figure 6:
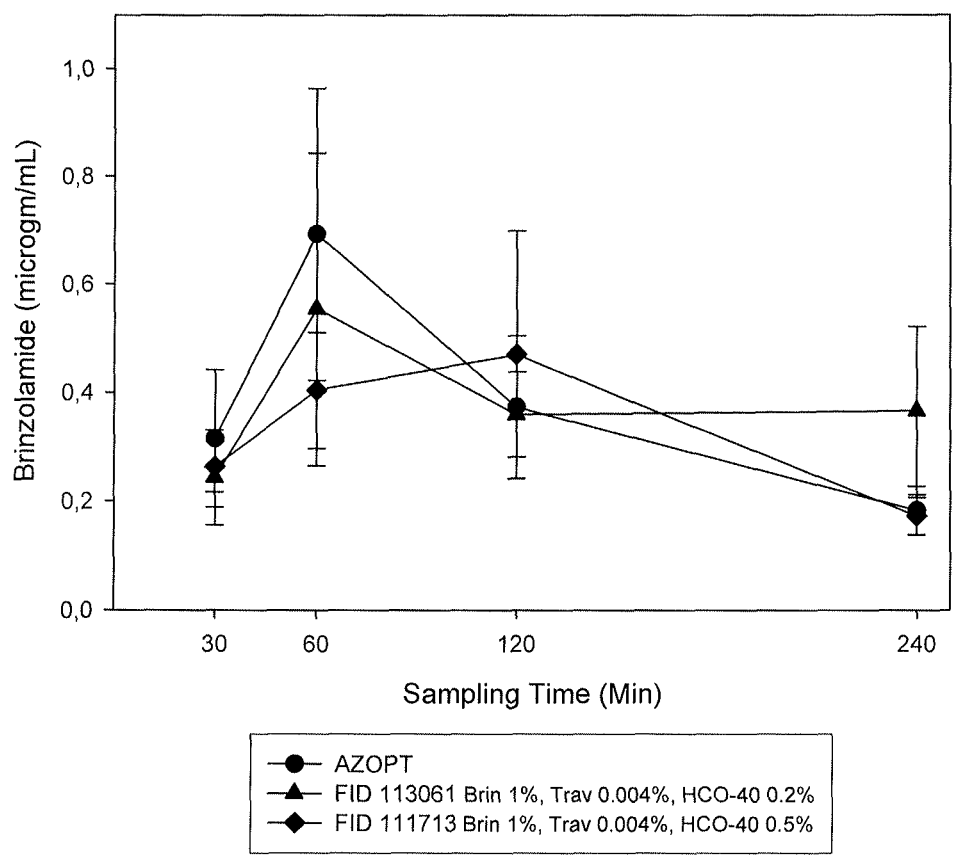
FIG. 6 is an exemplary graph of concentration of therapeutic agent (i.e., carbonic anhydrase inhibitor) at a biological target versus time in accordance with an aspect of the present invention.

With reference to FIG. 3, it can be seen that the concentration of travoprost in the aqueous humor of rabbits was significantly greater for composition R than it was for composition T or for a composition that includes a same or similar level of a single therapeutic agent travoprost in combination with HCO-40 at a concentration of 0.5 w/v %. With reference to FIG. 4, it can be seen that the concentration of travoprost in the aqueous humor of rabbits was significantly greater for composition S than it was for composition U or the composition that includes a same or similar level of a single therapeutic agent (travoprost) in combination with HCO-40 at a concentration 0.5 w/v %. With reference to FIG. 5, it can be seen that the concentrations of brinzolamide in the aqueous humor of rabbits showed a difference that is considered small for composition R than it showed for composition T or a composition that includes a same or similar level of a single therapeutic agent brinzolamide in combination with HCO-40 at a concentration of 0.5 w/v %. With reference to FIG. 6, it can be seen that the concentrations of brinzolamide in the aqueous humor of rabbits showed a difference that is considered small for composition S than it showed for composition U or a composition that includes a same or similar level of a single therapeutic agent brinzolamide in combination with HCO-40 at a concentration of 0.5 w/v %.

I claim:

1. An aqueous ophthalmic pharmaceutical solution composition suitable for topical application to an eye of a human, comprising:
   a prostaglandin suitable for lowering intraocular pressure of the eye, the prostaglandin being in the composition at a concentration that is at least 0.001 w/v % but less than 0.01 w/v %;
   a surfactant in the composition at a concentration that is at least 0.03 w/v % but less than 0.3 w/v %, wherein:
   i. the surfactant is entirely ethoxylated and/or hydrogenated vegetable oil and the ethoxylated and/or hydrogenated castor oil is the only surfactant in the composition; and
   ii. the composition is free of benzalkonium chloride; and
   a polymeric quaternary ammonium compound in the composition at a concentration that is greater than 0.0003 w/v % but less than 0.003 w/v %; and
   water.

2. A composition as in claim 1 wherein concentration of the surfactant in the composition is less than 0.15 w/v %.

3. A composition as in claim 1 wherein the prostaglandin is travoprost.

4. A composition as in claim 1 wherein the prostaglandin and the surfactant are non-ionic.

5. A composition as in claim 1 wherein the surfactant is entirely ethoxylated or hydrogenated vegetable oil.

6. A composition as in claim 1 wherein the surfactant is entirely castor oil.

7. A composition as in claim 1 wherein the surfactant is entirely Polyoxyl 40 Hydrogenated castor Oil.

8. A composition as in claim 1 wherein the composition satisfies Ph. Eur. A, Ph. Eur. B or both.

9. A composition as in claim 1 wherein the composition is substantially free of any chloride containing agents.

10. A composition as in claim 1 wherein the prostaglandin is in the composition at a concentration of less than 0.006 w/v %.

11. A composition as in claim 1 wherein the composition is disposed in an eye dropper.

12. A composition as in claim 4 wherein the surfactant is entirely ethoxylated and/or hydrogenated vegetable oil.

13. A composition as in claim 12 wherein the surfactant is entirely castor oil.

14. A composition as in claim 13 wherein the prostaglandin is in the composition at a concentration of less than 0.006 w/v %.

15. A composition as in claim 14 wherein the composition satisfies Ph. Eur. A, Ph. Eur. B or both.

16. A composition as in claim 14 wherein the prostaglandin is travoprost.

17. A composition as in claim 16 wherein the surfactant is entirely Polyoxyl 40 Hydrogenated castor Oil.

18. A composition as in claim 17 wherein the composition is disposed in an eye dropper.

19. A composition as in claim 18 wherein concentration of the surfactant in the composition is less than 0.15 w/v %.

20. A composition as in claim 18 wherein concentration of the polymeric quaternary ammonium compound in the composition is greater than 0.0007 w/v % but less than 0.0015 w/v % of the pharmaceutical composition.

21. A composition as in claim 1 wherein concentration of the polymeric quaternary ammonium compound in the composition is greater than 0.0007 w/v % but less than 0.0015 w/v % of the pharmaceutical composition.

22. A composition as in claim 1 wherein the polymeric quaternary ammonium compound is polyquaternium-1.

23. A composition as in claim 20 wherein the polymeric quaternary ammonium compound is polyquaternium-1.

* * * * *